(12) United States Patent
Namba

(10) Patent No.: US 6,613,039 B1
(45) Date of Patent: Sep. 2, 2003

(54) SAFETY GUIDE FOR SURGICAL PLACEMENT OF SHARP INSTRUMENTS

(75) Inventor: Robert S. Namba, 321 Milford Dr., Corona Del Mar, CA (US) 92625

(73) Assignee: Robert S. Namba, Corona Del Mar, CA (US)

( * ) Notice: Subject to any disclaimer, the term of this patent is extended or adjusted under 35 U.S.C. 154(b) by 36 days.

(21) Appl. No.: 09/697,463

(22) Filed: Oct. 26, 2000

(51) Int. Cl.[7] ............................ A61M 1/00; A61M 27/00
(52) U.S. Cl. ........................... 604/541; 604/160; 606/54
(58) Field of Search ............................. 604/19, 21, 27, 604/46, 47, 48, 93.01, 115–117, 158, 160, 161, 162, 164.01, 165.01, 165.02, 165.04, 166.01, 187, 971, 198, 264, 272, 523, 533–535, 538, 540.1, 541; 606/108, 131, 151, 167, 172, 96, 98, 54–55, 59, 104; 128/DIG. 6, 26, 917, 919

(56) References Cited

U.S. PATENT DOCUMENTS

| | | | |
|---|---|---|---|
| 2,393,143 A | | 1/1946 | Carwile |
| 2,566,145 A | | 8/1951 | Sandula |
| 4,257,411 A | * | 3/1981 | Cho .............................. 606/96 |
| 4,535,768 A | | 8/1985 | Hourahane et al. |
| 4,576,589 A | | 3/1986 | Kraus et al. |
| 4,602,898 A | | 7/1986 | Brown et al. |
| 4,612,921 A | * | 9/1986 | Lazo de Zbikowski ....... 606/72 |
| 4,823,780 A | * | 4/1989 | Odensten et al. .......... 408/72 B |
| 4,901,711 A | * | 2/1990 | Goble et al. ................... 606/97 |
| 5,152,764 A | | 10/1992 | Goble |
| 5,158,406 A | | 10/1992 | Ulinskas |
| 5,232,440 A | | 8/1993 | Wilk |
| 5,308,352 A | * | 5/1994 | Koutrouvelis ................ 604/116 |
| 5,330,468 A | * | 7/1994 | Burkhart ....................... 606/96 |
| 5,575,801 A | * | 11/1996 | Habermeyer et al. ........ 606/148 |
| 5,584,852 A | | 12/1996 | Parkola |
| 5,601,568 A | | 2/1997 | Chevillon et al. |
| 5,613,971 A | | 3/1997 | Lower et al. |
| 5,634,934 A | | 6/1997 | Yoon |
| 5,688,249 A | * | 11/1997 | Chang et al. ........... 604/164.01 |
| 5,688,253 A | | 11/1997 | Paradis |
| 5,690,645 A | | 11/1997 | Van Erp |
| 5,743,882 A | | 4/1998 | Luther |
| 5,743,909 A | | 4/1998 | Collette |
| 5,833,691 A | | 11/1998 | Bimman |

* cited by examiner

*Primary Examiner*—LoAn H. Thanh
(74) *Attorney, Agent, or Firm*—Knobbe, Martins, Olson & Bear, LLP

(57) ABSTRACT

A method and apparatus for the safe surgical placement of sharp instruments, such as trocars, is provided. The apparatus includes a safety guide that allows placement of a surgical trocar through a patient's skin and into a receiver. After placement of a sharp end of the trocar into the receiver, the trocar is then advanced through the patient's skin and removed from the body, thereby pulling a surgical drain, which is attached to the trocar, through the skin. The trocar and safety guide may then be disposed, the sharp end of the trocar remaining safely covered by the receiver.

20 Claims, 10 Drawing Sheets

SAFETY GUIDE FOR SURGICAL PLACEMENT OF SHARP INSTRUMENTS

BACKGROUND

The present invention relates to safety devices for surgical instruments. More specifically, the present invention relates to a device that advances the tip of a sharp surgical instrument, such as a trocar, through a patient's skin.

The implementation of safety measures in the workplace of healthcare personnel, such as physicians, nurses, and phlebotomists, has lagged behind such implementation in other industries. Devices are now available that diminish the exposure of healthcare personnel to puncture wounds and contamination by potentially dangerous or chemicals or body fluids, which may lead to infection by such pathogens as human immunodeficiency virus (HIV), hepatitis B, and hepatitis C. These devices include convenient safety sheaths around hypodermic needles, and intravenous medication bottles that do not require the use of hypodermic needles.

The nature of surgical procedures, however, unavoidably exposes medical personnel, including surgeons, assistants, and nurses, to many sharp and potentially injurious instruments. These instruments include scalpels, needles, retractors, and many other sharp and pointed tools. One of the most dangerous of these tools is the trocar, utilized, for example, to make stab wounds in the skin for placement of surgical drains. Surgical drains are used in a wide variety of surgical procedures. One end of such a drain is placed in a body cavity, and the other end extends outside of the patient's body, facilitating the removal of an unwanted collection of fluid, such as serum, blood, bile, and/or pus. The drain, generally made of plastic or rubber tubing, exits the body through a stab wound in the skin, draining the contents of the body cavity into a reservoir attached to the other end of the drain tube.

Most surgical drains are inserted through the skin with trocars, which are metallic spears that are attached to the plastic or rubber surgical drains. The trocars are extremely sharp and often unwieldy instruments, utilized to impale soft tissues around a body cavity. A trocar enters the patient's skin from inside the body cavity and exits out of the body cavity through the overlying skin. Great care must be taken in avoiding injury to vital structures while the trocar is being inserted. This procedure is often made difficult when a patient's tissues are thick or when slippery fluids and fat make handling of the smooth, metallic trocars difficult. The greatest risk to healthcare personnel occurs when the tip of the trocar exits the patient's skin. The exit site on the skin surface for the trocar tip must be predicted, and then the tip of the trocar must then be retrieved with a gloved hand after the trocar has protruded through the skin. The trocar is then pulled away from the patient's skin for approximately one or two feet, pulling the plastic or rubber tubing of the surgical drain through the stab wound along with the trocar. The drain is then cut, and the sharp trocar is then handed off to a scrub nurse for safe disposal. At every point in this drain-placement procedure, the surgical team is at risk for puncture wounds, and consequent infection, from the trocar.

SUMMARY

Thus, there is a need for a safety device that guides a trocar (or other sharp instrument) as it is being inserted through the skin, from within a patient's body cavity to the exterior surface of the skin, such that the trocar will be safely covered with a protective covering upon exit of the trocar from the skin.

One aspect of the invention includes a safety guide for placement of a trocar through the skin of a patient. The safety guide includes a "holder," adapted to releasably hold the trocar, and a "receiver," adapted to receive the sharp end of the trocar. The holder and the receiver are aligned such that the sharp end of the trocar is insertable through the patient's skin and then into the receiver while the trocar is releasably held by the holder.

In one embodiment, the holder is adapted to allow the trocar to slide longitudinally through it, while the trocar is releasably held by the holder. In some embodiments, the holder and the receiver are substantially immovable with respect to each other.

In a preferred arrangement, the receiver comprises a substantially cylindrical tube, forming a "sheath." In further arrangements, the receiver may be and/or act as a pad or "cushion," into which the sharp end of the trocar is placed. In this embodiment, the receiver may be made of one or more of the following materials: soft plastic, rubber, urethane, polyurethane, and polystyrene. Other materials may be used as appropriate, and will be apparent to those of skill in the art.

In another aspect, the safety guide includes a first tube, as well as a second tube that is slideably inserted into or around the first tube. A receiver, adapted to receive a sharp end of the trocar, is attached to the first tube. A holder, adapted to releasably hold the trocar, is attached to the second tube. The holder and the receiver are aligned such that the sharp end of the trocar is insertable through the patient's skin and then into the receiver while the trocar is releasably held by the holder.

In a preferred embodiment, a surgical drain is attached to the trocar or other sharp surgical instrument. In further embodiments, the holder and/or receiver is advantageously attached to its respective tube by a strut. In some embodiments, the first and second tubes are noncylindrical, i.e., asymmetrical in cross-sectional shape, such that the first tube cannot substantially rotate about the longitudinal axis of the second tube when the second tube is slideably inserted into or around said first tube. This mechanism provides nonrotatable alignment of the holder and the receiver, which facilitates placement of the sharp end of the trocar into the receiver.

In certain preferred arrangements, the receiver, such as a sheath, is substantially housed within the strut. In other arrangements, the receiver is adapted to allow the surgical instrument to lock releasably with the sheath. This can occur if, for example, a portion of the receiver is configured to fit into a recess in the outer surface of the trocar.

The holder may have a longitudinal slot along its length. This slot allows removal of the trocar or surgical drain from the holder, directly through the slot. A slot piece may also be provided, which is attached to and rotatable within the instrument holder. This slot piece is, in some embodiments, substantially cylindrical and also has a longitudinal slot, which is alignable with the longitudinal slot in the holder, in order to facilitate removal of the trocar or surgical drain.

Another aspect of the invention comprises a surgical trocar that is an elongate rod having a sharp end and a recess in the outer surface of the rod. This recess is configured to fit into the holder of the safety device. The recess may extend partially or totally around the circumference of the outer surface of the rod.

Another aspect of the invention includes a method of protecting surgical personnel from puncture wounds during placement of a surgical drain. This includes the following:

(a) providing a safety guide having first and second ends; (b) placing the first end of the safety guide outside a patient's skin, the first end having a receiver; (c) placing the second end of the safety guide through a surgical incision into a body cavity, the second end releasably holding a trocar; (d) moving the receiver and the trocar closer to each other, thereby puncturing the skin with the trocar; and (e) further moving the receiver and the trocar closer to each other, thereby inserting the trocar into the receiver.

In one embodiment, the step of moving the receiver and the trocar closer to each other is accomplished by moving the first end and the second end of the safety guide closer to each other.

In an alternative embodiment, the first end and the second end of the safety guide may remain fixed relative to each other, such as in a "C-arm" configuration. Indeed, in this embodiment the safety guide may be made from a single piece of material if desired. To penetrate the patient's skin with the trocar, and then to insert the sharp end of the trocar into the receiver, the surgeon advantageously slides the trocar through the second end of the safety guide, which is slideably holding the trocar. As the surgeon continues to slide the trocar through the second end of the safety guide, which is positioned within the body cavity, the trocar penetrates the patient's skin, from the inside to the outside of the skin. Then, as the surgeon further slides the trocar through the second end of the safety guide, the sharp end of the trocar, which is outside the skin, is inserted into the receiver, e.g., a sheath, in the first end of the safety guide.

Further embodiments of the method include any or all of the following: (1) locking the sharp end of the surgical instrument within the receiver; (2) removing the sharp instrument from the patient's body, while at least the sharp end of the instrument is covered by the receiver; (3) pulling a portion of the surgical drain through a stab wound, made by the trocar, from inside the patient's body to the outside; (4) removing the sharp instrument from the drain after one end of the drain is outside the patient's body cavity and while the other end of the drain remains inside the patient's body; and (5) disposing of the sharp instrument, while at least the sharp end of the instrument is covered by the sheath.

Another aspect of the invention comprises a kit that includes a safety guide according to the present invention and a sharp instrument having a sharp end configured to fit into the sheath of the safety guide. In another embodiment, the kit comprises a safety guide, which is adapted to releasably hold a trocar at on end of the safety guide, and which has a receiver for the trocar at the other end of the safety guide. The kit further comprises instructions for use.

Further features and advantages of the invention will become apparent to one of skill in the art in view of the detailed description of the preferred embodiment which follows, when considered together with the attached drawings and claims.

DETAILED DESCRIPTION OF THE PREFERRED EMBODIMENTS

Figure 1:
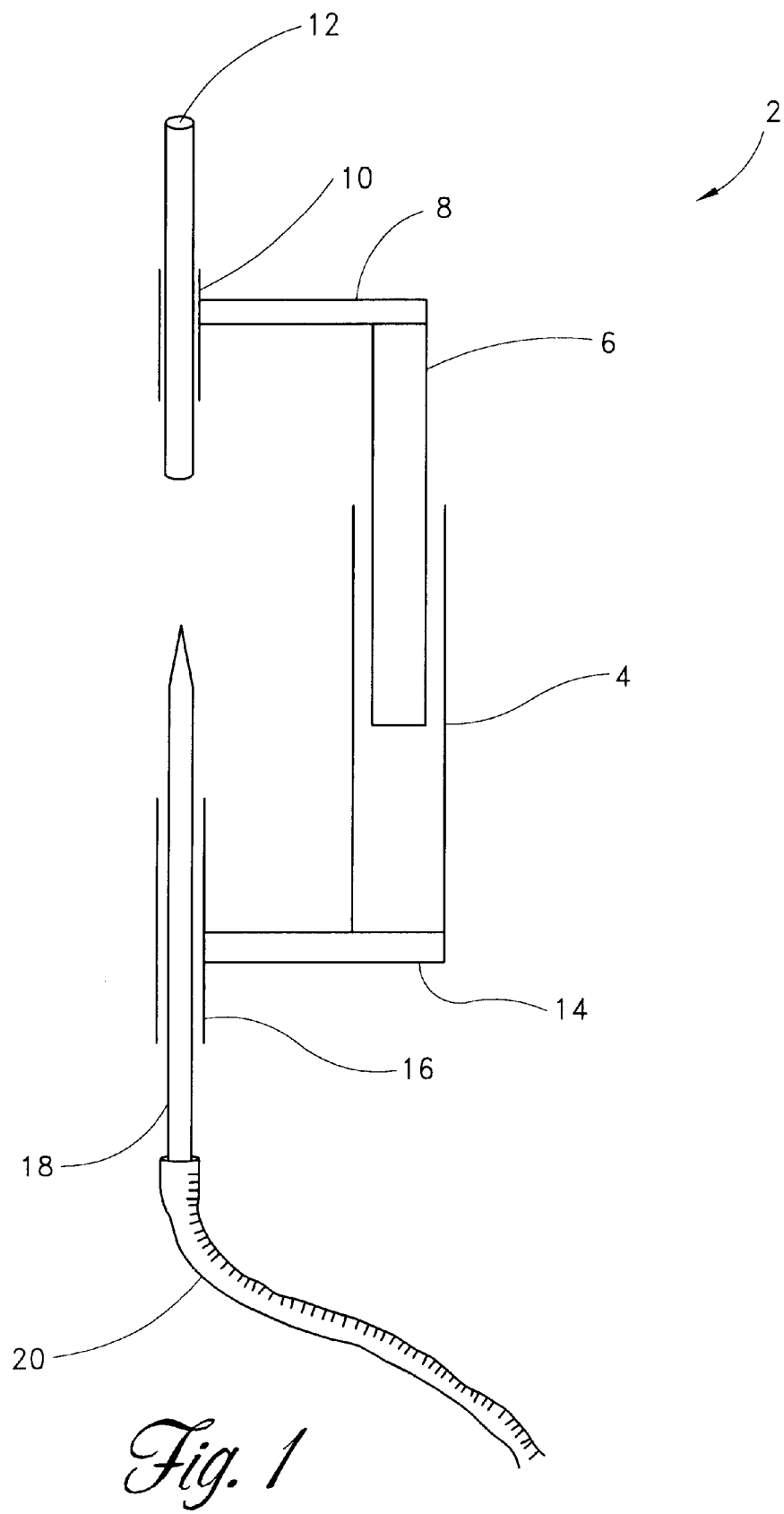
FIG. 1 is a schematic side elevational view of a safety guide device with a surgical trocar, drain, and safety sheath.

FIG. 1 shows a safety guide 2 in accordance with one aspect of the invention. Other aspects of the invention using any combination of the features disclosed will be readily apparent to one of skill in the art in view of the disclosure herein.

Figure 9:
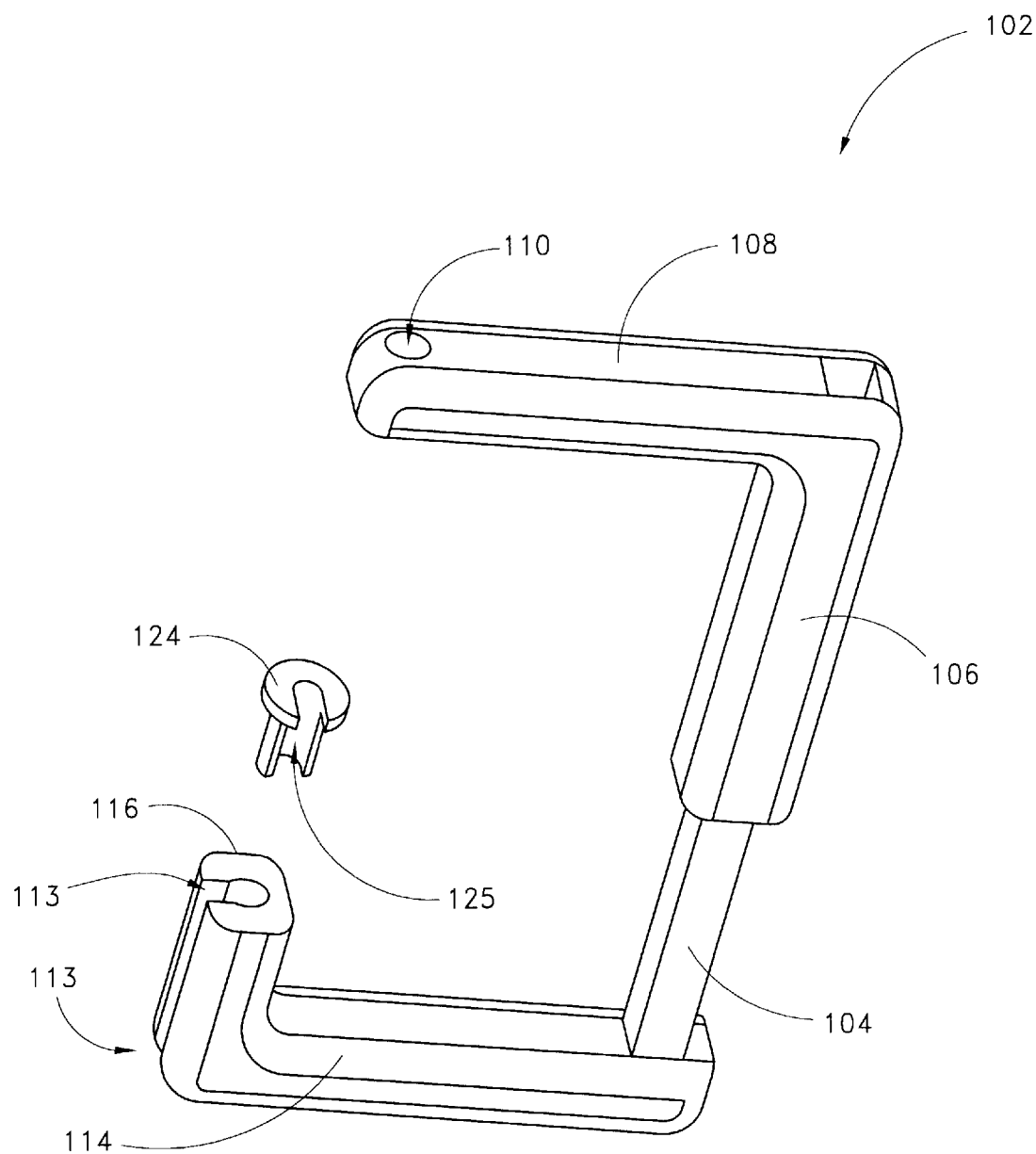
FIG. 9 is an oblique elevational view of an alternative embodiment of the safety guide with a rotatable slot piece.

As shown in FIG. 1, in one embodiment the safety guide 2 includes a bottom tube 4 and a top tube 6, which slideably fits inside the bottom tube 4. Alternatively, as shown in FIG. 9, the top tube 106 may have a larger cross-sectional area than the bottom tube 104, and thus the bottom tube 104 can slideably fit within the top tube 106. Regardless of which tube fits into the other, in this embodiment the tubes are preferably freely connectable, slideable with respect to each other, and disconnectable.

In the embodiment shown in FIG. 1, as the top tube 6 is slideably inserted in the bottom tube 4, a trocar 18 or other sharp surgical instrument is advantageously held fixed with respect to the bottom tube and is thereby inserted into the sheath 12. Note that the trocar 18 will also be referred to herein as a sharp instrument 18, to make it clear that this invention is intended to be applicable not only to trocars, but also to other tissue-piercing surgical instruments having sharp points.

Although the description of the embodiments disclosed herein refer to a top tube 6 and bottom tube 4, these "tubes" need not be cylindrical, i.e., circular in cross-sectional shape, although they can be. In addition to a circle, alternative cross-sectional shapes of these tubes include an ellipse, a triangle, a rectangle, or other polygon. In fact, asymmetry or eccentricity of any kind in the cross-sectional shape of the tubes is preferred to ensure that, as the top tube 6 slideably inserts into the bottom tube 4, the top tube 6 cannot rotate about the longitudinal axis of the bottom tube 4. This helps assure proper, nonrotational alignment of the trocar 18 and sheath 12 as the former is inserted into the latter.

Further, one of the "tubes," either the top tube 6 or bottom tube 4, need not be hollow or otherwise contain a central cavity, or lumen. For example, in the embodiment illustrated in FIG. 10, the bottom tube 4 can be solid, i.e., non-hollow. In this case, the bottom "tube" can actually be a rod or other similar, solid structure. The top tube 6 in the embodiment illustrated in FIG. 10, however, should preferably contain a central cavity or lumen in order to allow the bottom tube 4 to slide within the top tube 6.

The length of the top tube 6 and bottom tube 4 may advantageously be in the range of 3 to 30 cm, depending on the type of surgery to be performed. For abdominal general surgery or orthopedic surgery, or surgery for obese persons, a longer tube length may be preferred because of the large incision size and the relatively large thickness of skin and subcutaneous fat. In contrast, smaller tube sizes may be desirable in, for example, ophthalmologic, otolaryngologic, or plastic surgical procedures, in which incision sizes and tissue thicknesses are often less than in the former surgery types. In a preferred embodiment, the lengths of the top tube 6 and bottom tube 4 are in the range of 12 to 25 cm.

FIG. 1 further shows a sheath holder 10, attached to the top tube 6 by a top strut 8. The top strut 8 is generally perpendicular to the top tube 6 and the sheath holder 10 in one aspect of the invention. Thus, the sheath holder 10 is parallel to the top tube 6. Other orientations may be provided and will be readily apparent to one of skill in the art. For example, the sheath holder 10 may be directly attached to the top tube 6, without the need for an intervening top strut 8. Such orientations are possible if, for example, the top tube 6 is curvilinear, or "bow-shaped," such that the top tube 6 may connect to both the bottom tube 4 (at one end of the top tube 6) and the instrument holder 16 (at the other end of the top tube 6) (not illustrated).

The safety guide 2 can be made from any of a variety of materials, including metals or plastic. In certain preferred arrangements, one or more components of the safety guide 2, such as the sheath holder 10, top tube 6, top strut 8, instrument holder 16, bottom tube 4, and bottom strut 14, may advantageously be made of acrylonitrile butadiene styrene (ABS plastic). Further, a surgical grade of ABS plastic is preferred. Preferred dimensions of these parts are as follows: the sheath holder (10): 0.5–10 cm in length; top tube (6): 2–30 cm in length; top strut (8): 0–30 cm in length; instrument holder (16): 0.5–10 cm in length; bottom tube (4): 2–30 cm in length; and bottom strut (14): 0–30 cm in length. Other sizes for these parts are entirely compatible with and within the scope of the invention and will depend in part on the following factors among others, as will be readily appreciated by those of skill in the art: the type of surgery being performed, the size of the incision, the depth of the body cavity into which the drain is being placed, the caliber (diameter) of the surgical drain, and the thickness of the skin through which the trocar is being placed.

The sheath holder 10 can hold and, in some embodiments, release a safety sheath 12. The safety sheath 12 is advantageously cylindrical or substantially cylindrical in shape, and is preferably made of plastic, rubber, metal, or other suitable material that is somewhat soft and pliable, yet resists penetration by the sharp trocar 18. Plastic materials suitable for the sheath 12 include polytetrafluoroethylene (PTFE), polyurethane, and ABS plastic, as well as other plastics known to those of skill in the art.

As the configuration of the sheath holder 10 may be cylindrical in one aspect of the invention, the sheath 12 can fit within the lumen of the sheath holder 10, which is approximately 1 mm less in diameter than the sheath holder 10. In addition, the sheath holder 10 can be tapered in certain aspects of the invention. That is, the cross-sectional diameter of sheath holder 10 can be smaller at one of its ends than the other, causing the sheath holder 10 to be conical or frusto-conical in shape (not illustrated). This taper advantageously permits the sheath holder 10 to firmly hold the sheath 12 once the sheath 12 is slid snugly into the sheath holder 10.

Figure 5:
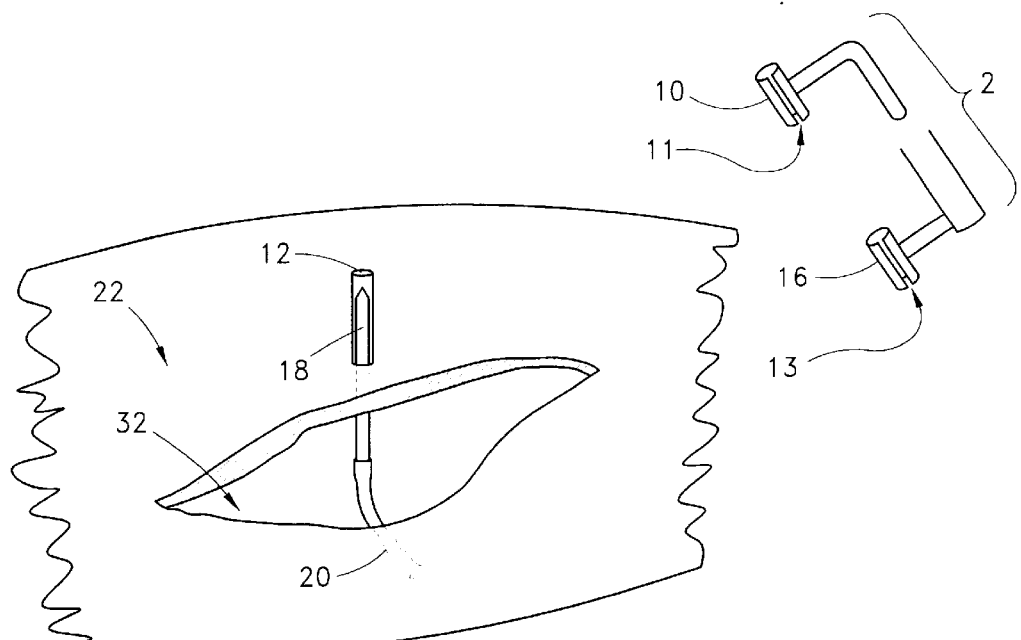
FIG. 5 is a schematic oblique elevational view of the safety guide as it is being removed from the patient after placement of the surgical trocar through the patient's skin.
Figure 5A:
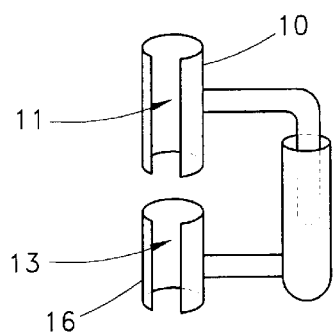
FIG. 5a is a schematic oblique elevational view of the safety guide with longitudinal openings present.

The ability of the sheath holder 10 to hold the sheath 12 stems from the sheath holder's 10 similarity in diameter to the diameter of the safety sheath 12 (preferably within 2 mm of each other), as well as the coefficient of friction that results from contact pressure between, and the compositional materials of, the sheath holder 10 and the safety sheath 12. The ability in some embodiments of the sheath holder 10 to release the held safety sheath 12 stems primarily from two factors: (1) the sheath holder's 10 material elasticity, particularly if the sheath holder 10 is made from flexible plastic or rubber; and (2) the presence, in some embodiments, of a longitudinal sheath opening 11, as shown in FIGS. 5 and 5*a*.

The bottom tube 4 is preferably connected, either directly or indirectly, to an instrument holder 16. The instrument holder 16 releasably holds a sharp instrument 18, such as a trocar. The mechanism for releasing the sharp trocar 18 from the instrument holder 16 is more fully explained below, in the description of FIG. 5*a*.

In one aspect of the invention, as shown in FIG. 1, the instrument holder 16 is parallel to the bottom tube 4, and is perpendicular to a bottom strut 14. The bottom strut 14 connects the bottom tube 4 to the instrument holder 16. Other orientations may be provided and will be readily apparent to one of skill in the art. For example, the instrument holder 16 may be directly attached to the bottom tube 4, without the need for an intervening bottom strut 14. Such an orientation is possible if, for example, the bottom tube 4 is curvilinear, or "bow-shaped," such that the bottom tube 4 may connect to both the top tube 6 (at one end of the bottom tube 4) and the instrument holder 16 (at the other end of bottom tube 4) (not illustrated).

FIG. 1 also shows a surgical drain 20, which is generally tubular and commonly made of rubber or plastic, and which is releasably attached to the trocar 18.

Figure 2:
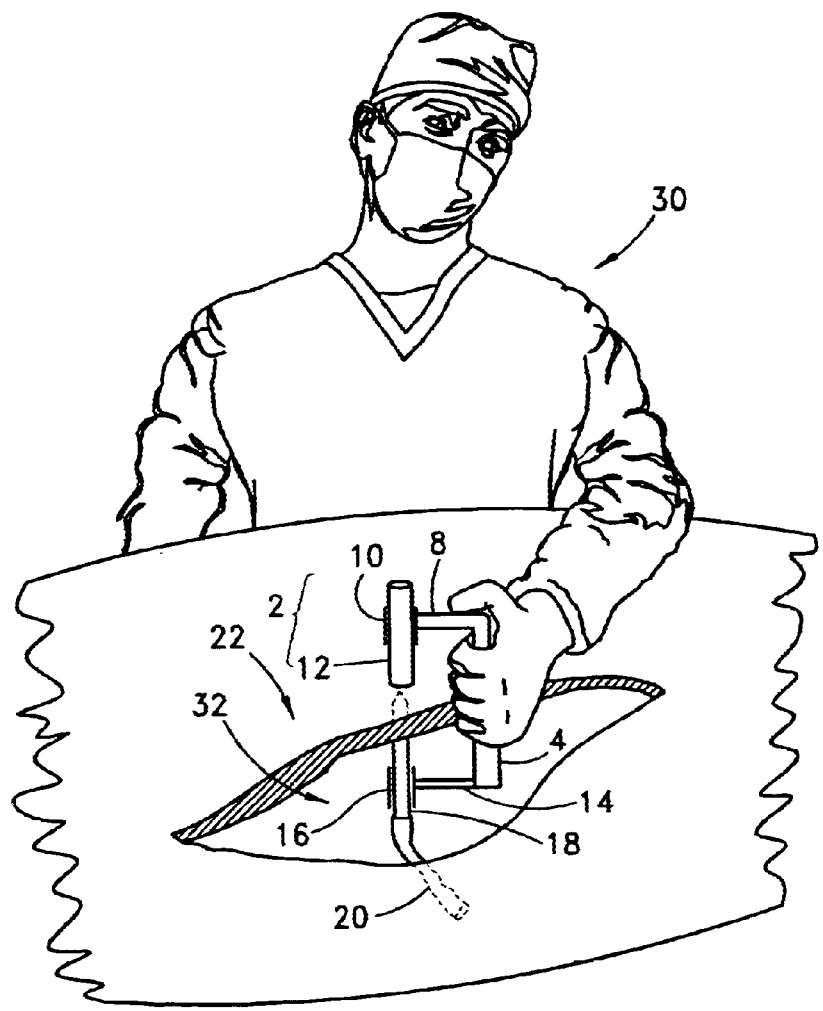
FIG. 2 is a schematic diagram of a surgeon placing a surgical trocar through a patient's skin using the safety guide.

FIG. 2 shows a surgeon 30 using the safety guide 2 to place a trocar 18 through the skin 22 of a patient. In positioning the safety guide 2, the surgeon 30 places the instrument holder 16 into an open surgical wound 32 of the patient. The surgeon 30 further positions the trocar 18 such that it lies deep, i.e., internal, to the skin 22 of the patient. The sheath holder 10 and sheath 12 are positioned superficial, i.e., external, to the patient's skin 22, in preparation for advancement of the trocar 18 through the skin 22 of the patient. To actuate or engage the safety guide 2, in one emodiment the surgeon 30 pushes the top strut 8 toward the bottom strut 14, thereby slideably inserting the top tube 6 (as shown in FIG. 1) into the bottom tube 4. Also shown is the surgical drain 20, which is attached to the trocar I 8. The end of the drain 20 that is not attached to the trocar 18 may be inside or outside the surgical wound 32 of the patient at the time of engagement of the safety guide 2.

Figure 3:
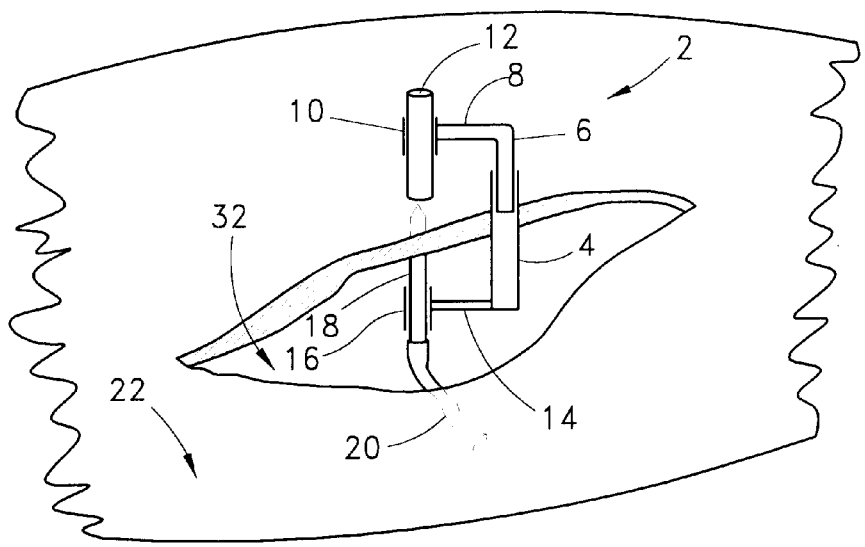
FIG. 3 is a schematic oblique elevational view of the safety guide in preparation for penetration of the surgical trocar through the patient's skin.

FIGS. 3–6 illustrate the operation of the safety guide 2 in placement of a surgical drain, according to one aspect of the invention, in four steps:

First, as shown in FIG. 3, the safety guide 2 is positioned by the surgeon such that the sheath holder 10 and the sheath 12 are positioned external to the patient's skin, and the trocar 18 and instrument holder 16 are positioned internal to the patient's skin 22, within the surgical wound 32. A surgical drain 20 is attached to the trocar 18. At this time, the free end of the surgical drain 20 may reside within the surgical wound 32 or outside of it. FIG. 3 shows the positional placement of the safety guide 2 prior to puncture of a patient's skin 22 by the trocar 18.

Figure 4:
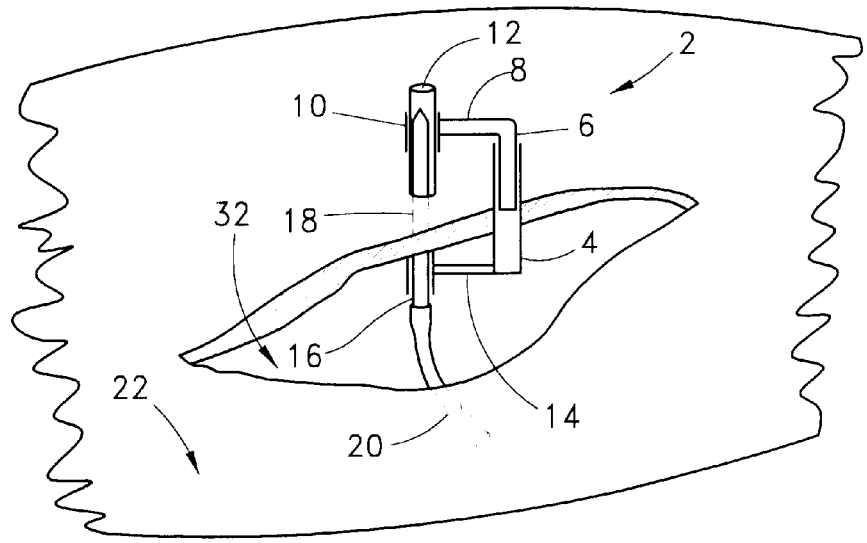
FIG. 4 is a schematic oblique elevational view of the safety guide after the surgical trocar has been placed through the patient's skin and into the safety sheath.

Second, the surgeon slideably moves the top tube 6 within the bottom tube 4, causing the top strut 8 to move closer to the bottom strut 14, as shown in FIG. 4. Alternatively, the bottom tube 4 can be slideably inserted into the top tube 6. The insertion of one tube into the other preferably occurs in response to motion of the surgeon's hand. In certain preferred embodiments, the surgeon pushes on the top strut 8 with his (or her) thumb, forcing the top strut 8 toward the bottom strut 14, while he holds the bottom tube 4 with his fingers wrapped around the bottom tube 4. There is precise alignment of the sheath holder 10 and the instrument holder 16, caused by the asymmetry in cross-sectional shape of top tube 6 and bottom tube 4. This asymmetry creates an antirotative mechanism that ensures that the top tube 6 cannot rotate about the longitudinal axis of the bottom tube 4, as discussed above. As a result of this alignment, the trocar 18 slides directly into the sheath 12 after the trocar 18 has punctured the patient's skin 22. FIG. 4 illustrates the safety guide 2 after puncture of the patient's skin 22 by the trocar 18.

After placement of the trocar 18 through the skin 22 of the patient, the sharp tip of the trocar 18 resides within the sheath 12, thus safely preventing it from exposing healthcare personnel to the risk of puncture wounds.

Third, the surgeon removes the safety guide 2 from the patient's wound 32. FIG. 5 illustrates removal of the safety guide 2 from patient while leaving behind the assembly of the safety sheath 12 and the trocar 18. In one aspect of the invention, the surgeon removes the sheath holder 10 from the sheath 12, by sliding the sheath holder 10 off of the sheath 12, such that the sheath 12 moves substantially only axially, i.e., along the longitudinal axis of the sheath 12, through the lumen (i.e., central cavity), of the sheath holder 10. This removal action leaves the sheath 12 attached to trocar 18.

In some embodiments the sheath holder 10 can have a longitudinal sheath opening 11 that spans the length of the sheath holder 10, and which facilitates removal of the sheath 12 from the sheath holder 10 by allowing the sheath 12 to "slip out of," i.e., move laterally through, the longitudinal sheath opening 11 in the sheath holder 10.

Figure 12:
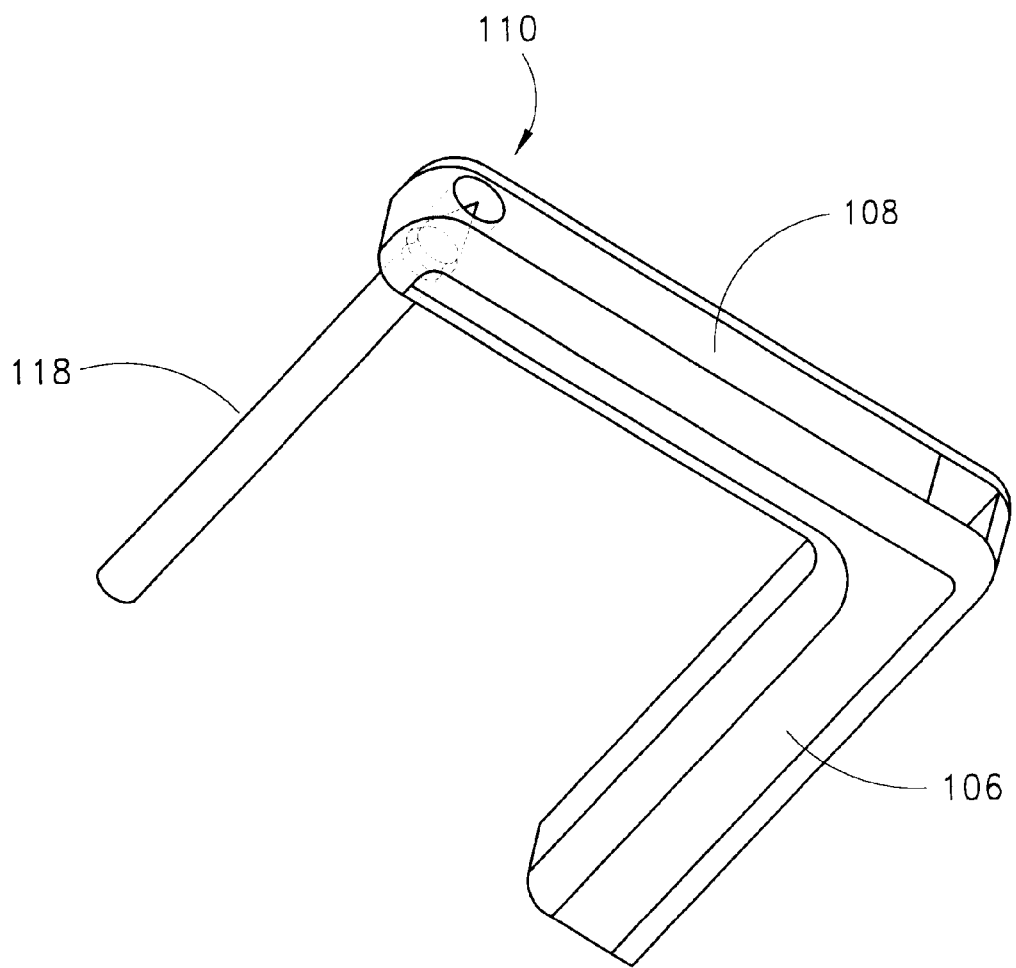
FIG. 12 is a side elevational view of a surgical trocar instrument and an alternative embodiment of the sheath holder.

In alternative embodiments of the invention, the sheath 12 is left "locked" in place within the sheath holder 10, which is housed within the top strut 8. This embodiment is illustrated in FIGS. 8 and 12 and is explained more fully below.

Similarly, removal of the surgical instrument holder 16 from the trocar 18 is accomplished, in one aspect of the present invention, by pulling the trocar 18 upward through the skin (from inside to outside). This causes the trocar 18 to move axially through the lumen of the instrument holder 16 until the trocar 18 resides entirely outside of the instrument holder 16, and, advantageously, even outside the patient's body, as shown in FIG. 6.

Figure 6:
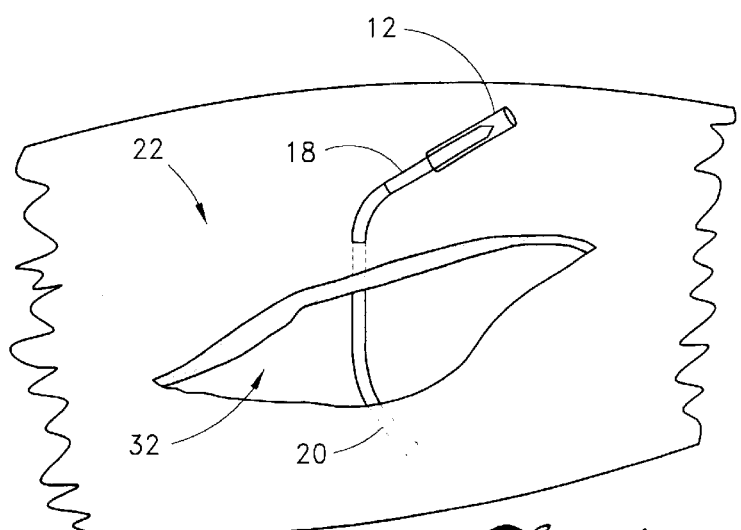
FIG. 6 is a schematic oblique elevational view of the surgical trocar and drain being withdrawn from the patient, after placement through the patient's skin.

At this time, the surgical drain 20, which is still attached to the trocar 18, lies partially in and partially out of the patient's body cavity and traverses the stab wound formed by the trocar 18, as shown in FIG. 6. The instrument holder 16 is then pulled out of the patient's wound 32 while allowing the surgical drain 20 to move axially through the lumen of the instrument holder 16, to free the instrument holder 16 from the surgical drain 20. To accomplish this, the end of the surgical drain 20 that lies within the patient's wound 32 may be temporarily pulled outside the patient's body in order to pull the instrument holder 16 away from the surgical drain 20 (not shown). In this embodiment, after the instrument holder 16 is freed from the surgical drain 20, the end of the surgical drain 20 that was just temporarily pulled outside the patient's body cavity is placed back inside the body cavity.

In an alternative embodiment, shown in FIG. 5a, a longitudinal instrument opening 13 that spans the length of the instrument holder 16 can be present, allowing the surgeon 30 to pull the trocar 18 and/or the surgical drain 20 out of the instrument holder 6 transversely, through the longitudinal instrument opening 13. In another embodiment, shown in FIGS. 9 and 10 and described below, the instrument holder 116 has a rotatable slot piece 124, which fits into the instrument holder 116. This rotatable slot piece 124 facilitates the alternate retention and release of the trocar 18 from the instrument holder 116.

Fourth, the surgeon pulls the trocar 18 and the sheath 12 entirely away from the patient's skin 22, and he pulls a portion of the length of the surgical drain 20 through the skin 22, placing the drain into final position. FIG. 6 illustrates the position of the trocar 18 and the sheath 12 as they are moved away from the patient's skin 22, while at the same time the surgical drain 20 is being pulled through the skin 22. Once a sufficient length of the drain 20 is pulled away from the patient's skin 22, typically approximately one or two feet, the trocar 18 is detached from the drain 20. This detachment occurs either by pulling the drain 20 off of the trocar 18 at the attachment point of the drain 20 to the trocar 18, or by cutting the drain 20 near its attachment to the trocar 18. Thereafter, one end of the drain 20 is external to the patient's skin 22 and lies outside of the patient's surgical wound 32. The other end of the drain 20 lies within the body cavity of the patient, inside the surgical wound 32.

During the aforementioned maneuvers, healthcare personnel are protected from puncture wounds while the trocar 18 is external to the patient's skin 22, i.e., after the trocar 18 has penetrated the patient's skin 22, because the sharp end of the trocar 18 is covered by the sheath 12.

In an alternative embodiment, the "holder" end (i.e., the end where an instrument holder is located) and "receiver" end (i.e., the end where a sheath or other trocar-receiving, protective structure is located) of the safety guide 2 may remain fixed relative to each other, such as in a "C-arm" configuration (not illustrated). If desired, the safety guide 2 may be made from a single piece of material in this embodiment. To penetrate the patient's skin with the trocar 18, and then to insert the sharp end of the trocar 18 into the receiver (e.g., a sheath), the surgeon advantageously slides the trocar 18 through the holder end of the safety guide 2, which slideably holds the trocar. As the surgeon progressively slides the trocar 18 through the holder end of the safety guide 2, which holder end is positioned within the body cavity, the trocar penetrates the patient's skin, from inside through outside. Then, as the surgeon slides the trocar 18 further through the holder end of the safety guide 2, the trocar is inserted into the receiver end of the safety guide 2.

Figure 7:
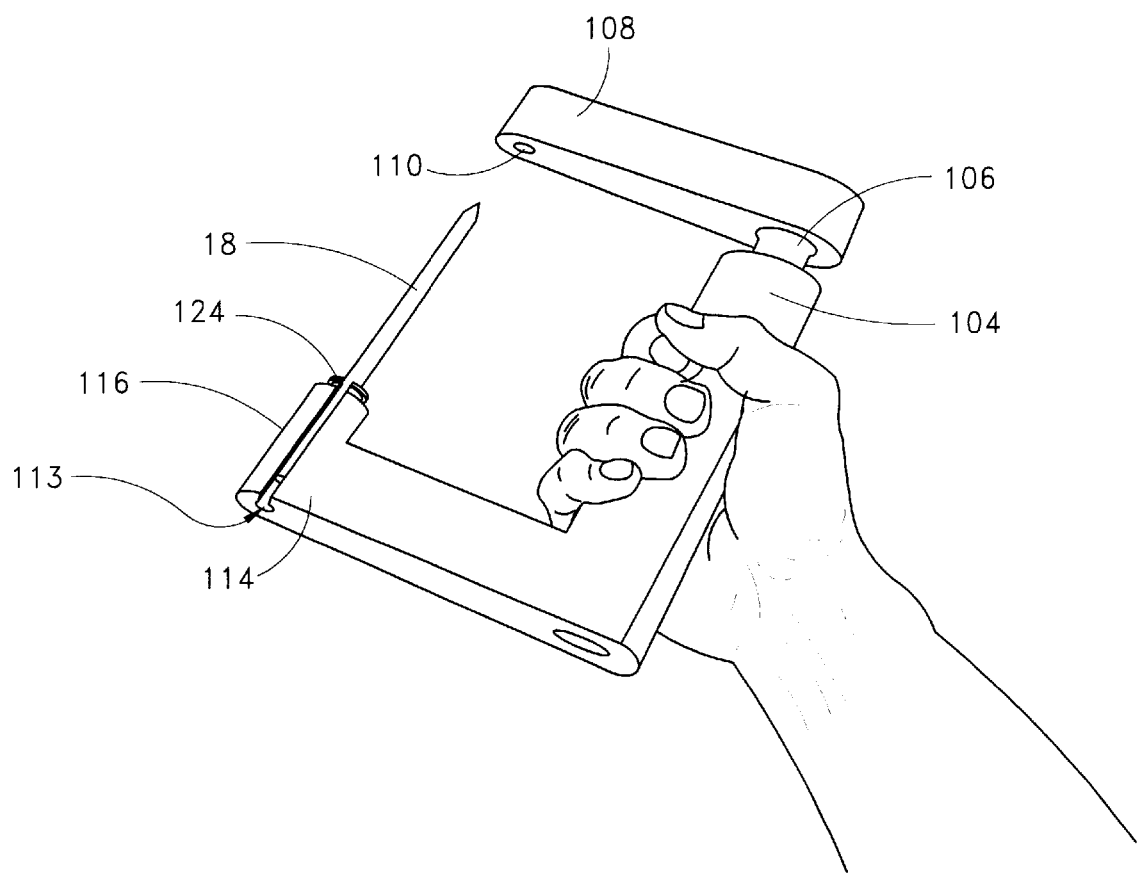
FIG. 7 is an oblique elevational view of an alternative embodiment of the safety guide, with the sheath holder housed within the top strut.

FIG. 7 illustrates an alternative embodiment of the safety guide, in which the sheath holder 110 is housed within the top strut 108. This design can be space-saving, as the entire length of the sheath holder need not extend beyond the width of the top strut 108. Furthermore, this arrangement can provide increased stability for the sheath holder 110 when the trocar 18 is inserted into the sheath holder 110.

Figure 8A:
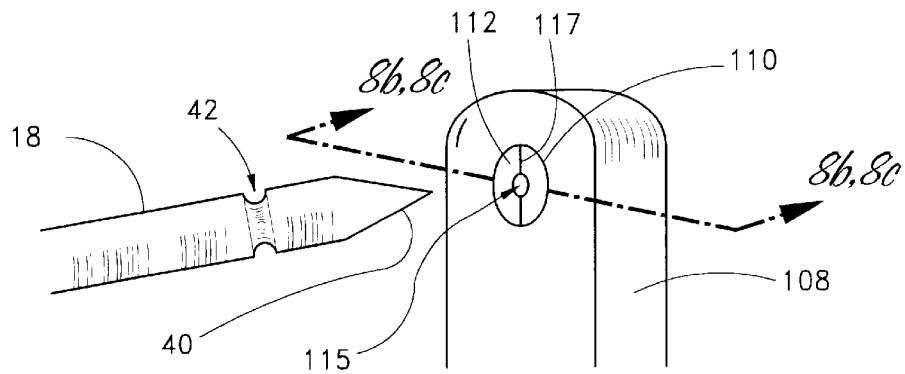
FIG. 8a is a side elevational view of a surgical trocar instrument and an alternative embodiment of the sheath holder.
Figure 8B:
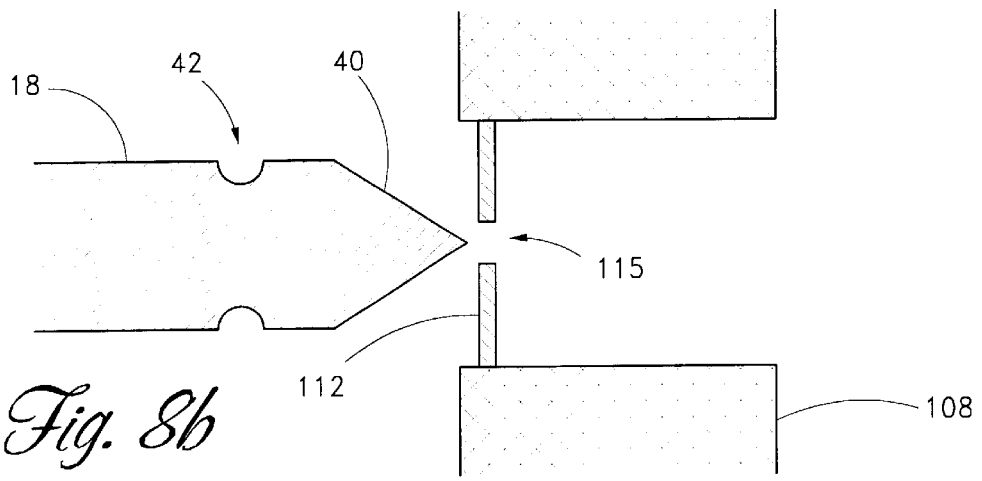
FIGS. 8b and 8c are schematic sectional views of the surgical trocar and a receiver mechanism in the safety guide.
Figure 8C:
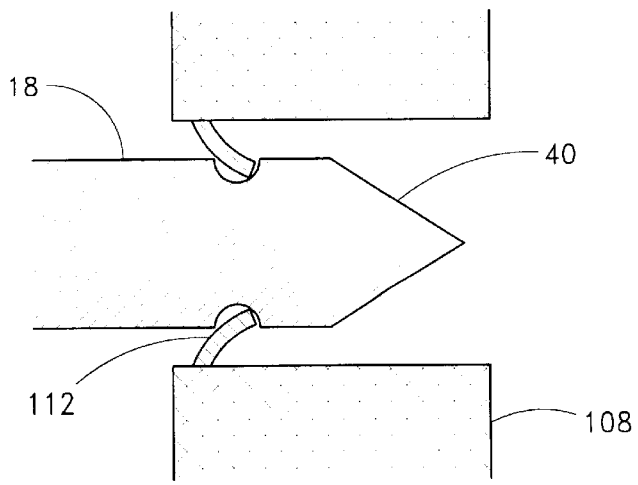

FIGS. 8a–c illustrate an alternative embodiment of the safety guide, in which the sheath holder 110 is housed within, or is integrated into, the top strut 108. The tip 40 of the trocar 18 fits into the sheath 112, which is in place within the sheath holder 110. In a preferred arrangement, the sheath 112 takes on the configuration of a "split washer" as illustrated in FIGS. 8a–c. As shown in FIGS. 8a and 8b, the sheath 112 may have a central seam 117, dividing two side portions of the sheath 112. The sheath 112 is preferably about 1 to 30 mm larger in diameter than the trocar 18. The two side portions of the sheath 112 on either side of the seam 117 move apart, advantageously under spring tension, when the tip 40 of the trocar 18 is inserted into a central hole 115 within the sheath 112 and the the tip 40 of the trocar 18 causes deflection of the two side portions of the sheath 112 on either side of the seam 117.

As the trocar 18 slides further into the sheath 112, a recess 42 on the surface of the trocar 18 becomes adjacent to the seam 117 of the sheath 112. When this occurs, the two side portions of the sheath 112 on either side of the seam 117 move closer to one another, again preferably under spring tension, and come to rest within the recess 42 of the trocar 18, as illustrated in FIG. 8c. This mechanism allows the trocar 18 to "lock" into place within the central hole 115 of the sheath 112; i.e., the two side portions of the sheath 112 on either side of the seam 117 remain within the recess 42 of the trocar 18, preventing the trocar from moving back out of the sheath 112. This prevents the trocar 18 from substantial translational movement along its longitudinal axis with respect to the sheath 112.

FIG. 12 shows an example of the trocar 18 situated in a "locked" position within the top strut 108. Once the trocar 18 is locked in place, the entire assembly of the top strut 108 and the trocar 18 can be disposed of as one unit, with the sharp tip 40 of the trocar 18 safely attached to, locked within, and shielded by the sheath 112.

In a preferred arrangement, the safety "receiver" of the trocar 18 is not a sheath, but is pad (not shown) that acts as a kind of "cushion" into which the sharp end of the trocar 18 is placed. In this embodiment, the receiver may be made of one or more of the following materials: soft plastic, rubber, urethane, polyurethane, and polystyrene. Other materials, especially other soft plastics, may be used as appropriate, and will be apparent to those of skill in the art.

Another aspect of the invention includes a sharp instrument 18, such as a surgical trocar, as illustrated in FIGS. 8a–c, which may be used in conjunction with the safety guide 2. The trocar comprises an elongate rod having two ends, one end being sharp. Near the sharp end, there is a recess 42 in the outer surface of the rod, and the recess is configured to fit into the sheath of the 112 of the safety guide 2. The recess 42 can be circumferential with respect to the outer surface of the rod, as shown in FIGS. 8a–c. Alternatively, the recess can be a notch or indentation in the outer surface of the rod that extends around less the entire circumference of the rod (not shown), such that the cross-sectional area of the rod is asymmetric.

FIG. 9 shows an alternative embodiment of the safety guide 102. The sheath holder 110 is recessed within the top strut 108. The bottom tube 104 can slide into the top tube 106. Also shown is the longitudinal instrument opening 113, which spans the length of the instrument holder 116. Further illustrated is a rotatable slot piece 124 with a longitudinal slot 125, which preferably spans the length of the rotatable slot piece 124.

Figure 10:
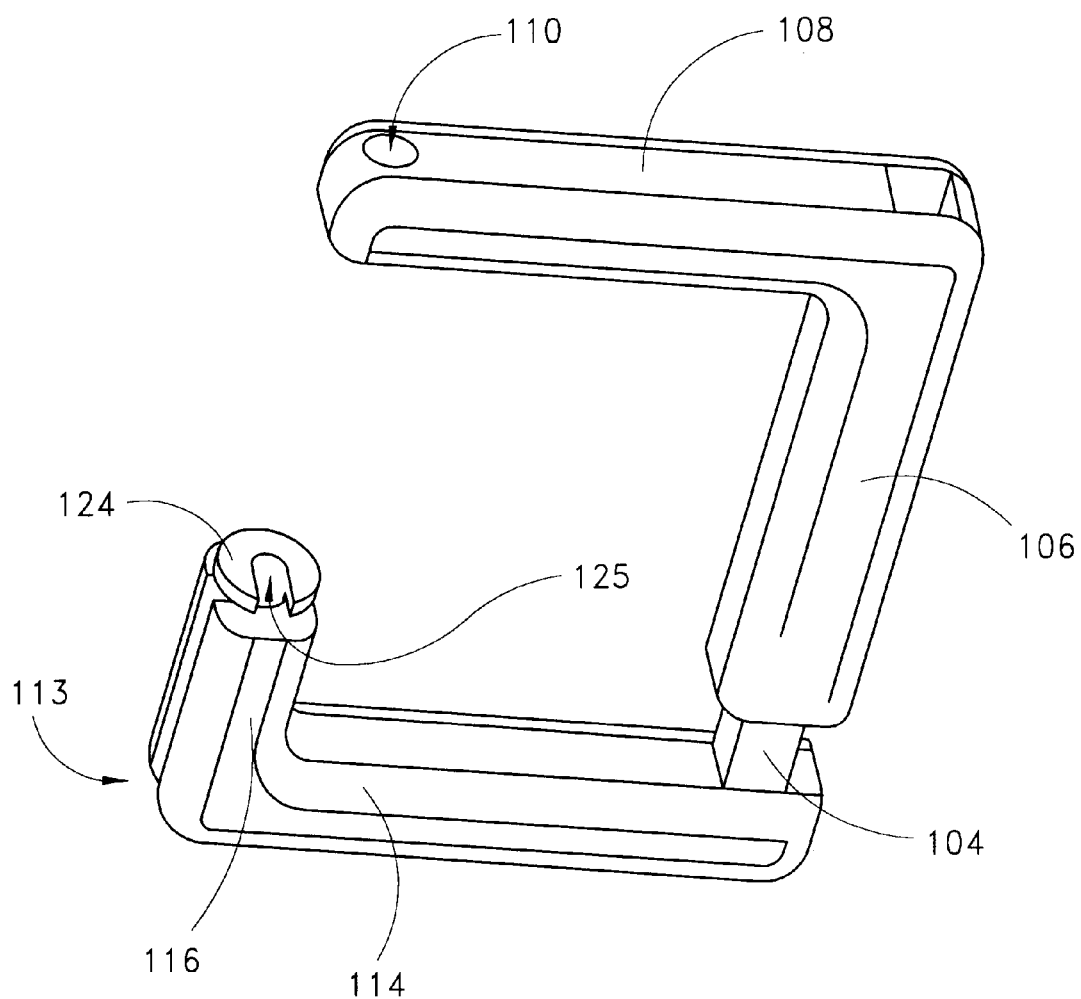
FIG. 10 is an oblique elevational view of an alternative embodiment of the safety guide with the rotatable slot piece.

As illustrated in FIG. 10, the rotatable slot piece 124 fits into the instrument holder 116. The slot piece 124 is rotatable within the instrument holder 116, such that the slot 125 within the slot piece 124 can align with the longitudinal instrument opening 113 in the instrument holder 116. This alignment facilitates removal of the surgical drain 20 from the instrument holder 116.

In this embodiment, once the surgeon pulls the trocar 18 axially out of the lumen of the instrument holder 116, he then rotates the slot piece 124 in order to align the slot 125 with the longitudinal instrument opening 113 in the instrument holder 116. In other words, the opening in the slot 125 within the slot piece 124 becomes confluent with the longitudinal instrument opening 113 in the instrument holder 116. Then, the surgeon can pull the surgical drain 20 out from the lumen of the instrument holder 116 laterally (sideways) toward the periphery (i.e., outer rim area) of the instrument holder 116, and the surgical drain 20 can thence be removed through both the slot 125 within the slot piece 124 and the longitudinal instrument opening 113 in the instrument holder 116. This mechanism allows free exit of the surgical drain 20 from the instrument holder 116. The bottom assembly, including the bottom tube 104 and the bottom strut 114, can then be freely removed from the patient's wound 32. In a preferred embodiment, these components are not reused and are discarded.

Conversely, when the slot piece 124 is rotated within the instrument holder 116 such that the slot 125 within the slot piece 124 is not aligned with the longitudinal instrument opening 113 in the instrument holder 116, as in the configuration illustrated in FIG. 10, the trocar 18 is prevented from "escaping" from the side of the instrument holder 116 and can thus be held in place within the instrument holder 116 while the trocar 18 is being inserted through the patient's skin 22.

Figure 11:
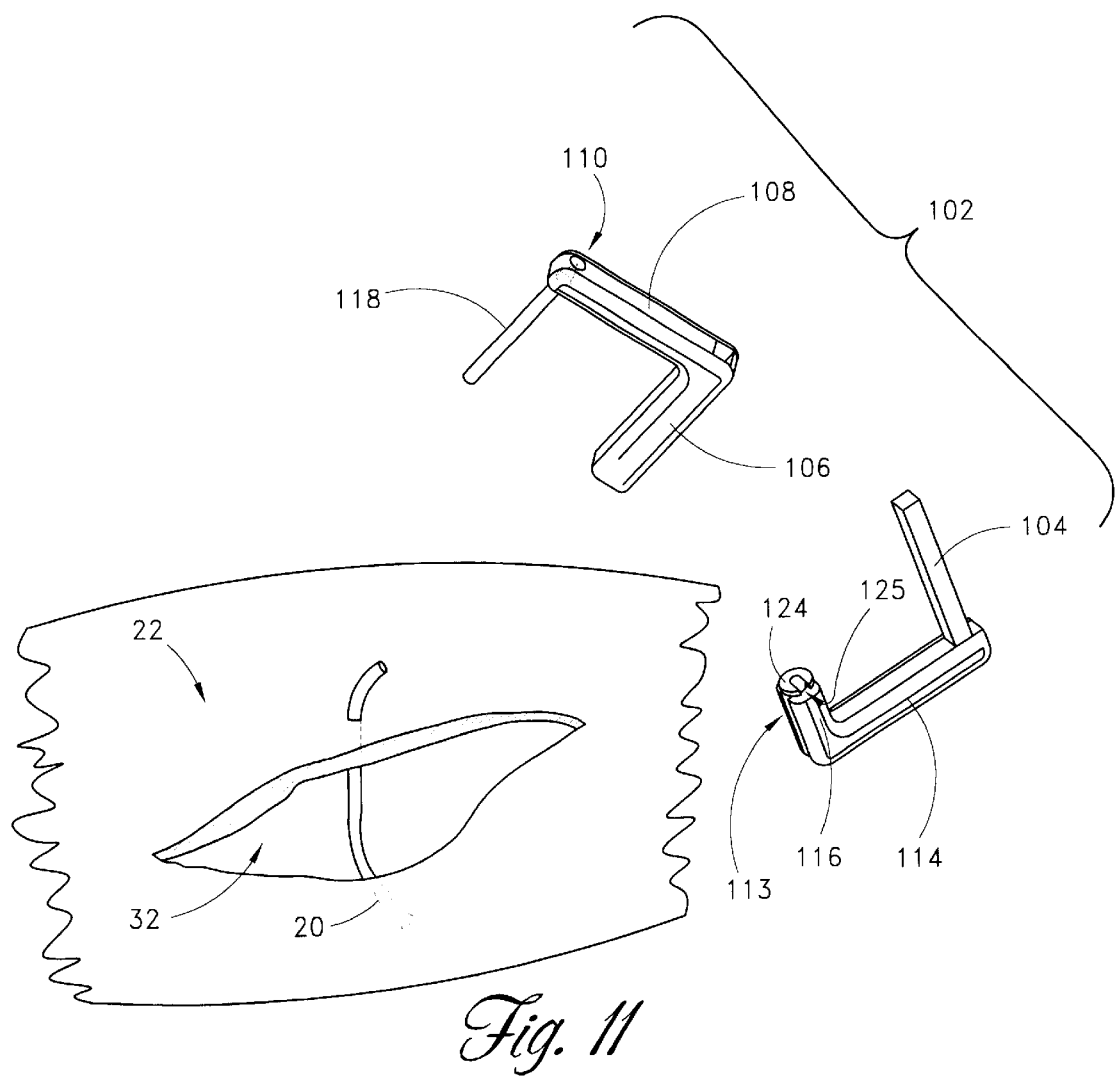
FIG. 11 is a schematic oblique elevational view of an alternative embodiment of the safety guide as it is being removed from the patient after placement of the surgical trocar through the patient's skin.

FIG. 11 illustrates removal of the alternative embodiment of the safety guide shown in FIGS. 9 and 10, including the top tube 106 and the bottom tube 104, from the patient's wound 32 and skin 22. The trocar 18 is locked into place within the sheath (not shown) and sheath holder 110. In this illustrated embodiment, the sheath holder 110 is housed within, or otherwise integrated into, the top strut 108.

Once the trocar 118 is locked in place within the top strut 108, as shown in FIG. 11, the entire top assembly, including the top tube 106, the top strut 108, and the trocar 18, which remains attached, or "locked," to the sheath holder 110, is pulled away from the patient's skin 22. This entire assembly is preferably discarded as one unit by a surgical nurse or operating room technician, with the trocar 18 still attached to, and covered by, the sheath holder 110. In this manner, once the trocar 18 is locked into place within the sheath and sheath holder 110, the trocar 18 is never removed from these protecting structures before it is discarded, so the risk of injury is kept low throughout the surgical procedure, the disposal process, and thereafter.

FIG. 12 illustrates the trocar 18 in place within the sheath (not illustrated) and the sheath holder 110. A detailed view of the of this assembly, particularly in the region of the sheath holder 110, is shown in FIGS. 8a–c.

Although this invention has been described in terms of certain preferred embodiments, other embodiments that are apparent to those of ordinary skill in the art are also within the scope of the invention. Accordingly, the scope of the invention is intended to be defined only by reference to the appended claims.

What is claimed is:

1. A safety guide for placement of a sharp instrument through the skin of a patient, comprising:

a first end having a holder adapted to releasably hold said sharp instrument; and a second end having a receiver adapted to receive a sharp end of said sharp instrument;

wherein said holder and said receiver are aligned such that the sharp end of said sharp instrument is insertable through the patient's skin and then into the receiver while the sharp instrument is releasably held by the holder; and wherein the holder has a first longitudinal slot that is open to alumen in the holder.

2. The safety guide of claim 1, further comprising a slot piece that is attached to and rotatable within the holder, said slot piece having a second longitudinal slot that is alignable with the first longitudinal slot in the holder.

3. The safety guide of claim 2, wherein the slot piece is releasably attached to the holder.

4. The safety guide of claim 1, wherein said receiver is adapted to allow said sharp instrument to lock with said receiver.

5. The safety guide of claim 4, wherein a portion of said receiver is adapted to fit into a recess in an outer surface of said sharp instrument.

6. The safety guide of claim 1, wherein the holder is adapted to allow the sharp instrument to slide longitudinally through the holder while the sharp instrument is releasably held by the holder.

7. The safety guide of claim 1, wherein the holder and the receiver are substantially rotatably immovable with respect to each other.

8. The safety guide of claim 1, wherein the receiver comprises a substantially cylindrical tube.

9. The safety guide of claim 1, wherein the receiver comprises a pad.

10. The safety guide of claim 9, wherein the receiver comprises a material selected from the group consisting of rubber, urethane, polyurethane, polystyrene, and other plastic.

11. The safety guide of claim 1, wherein the sharp instrument is a trocar.

12. A kit comprising:

the safety guide of claim 1; and an elongate rod having a sharp end configured to fit into said receiver.

13. A method of protecting surgical personnel from puncture wounds during placement of a sharp instrument through a patient's skin, comprising:

providing the safety guide of claim 1;

placing the first end of said safety guide outside said patient's skin, said first end having a receiver;

placing the second end of said safety guide through a surgical incision and into a body cavity, said second end adapted to releasably hold said sharp instrument;

moving said receiver and said sharp instrument closer to each other, thereby puncturing said patient's skin with said sharp instrument; and further moving said receiver and said sharp instrument closer to each other, thereby inserting said sharp instrument into said receiver.

14. A kit comprising:

a safety guide according to claim 1 comprising:
a holder adapted to releasably hold a sharp instrument;
a receiver adapted to receive a sharp end of said sharp instrument;

wherein said holder and said receiver are aligned such that the sharp end of said sharp instrument is insertable through a patient's skin and then into the receiver while the sharp instrument is releasably held by the holder; and instructions for use according to claim 13.

15. The method of claim 13, further comprising removing said sharp instrument from said patient's body, while at least a sharp end of said sharp instrument is covered by said receiver.

16. The method of claim 5, further comprising pulling a portion of a surgical drain from inside said patient's body to outside said body, said surgical drain having a first end and a second end, said first end being attached to said sharp instrument.

17. The method of claim 5, further comprising disposing said sharp instrument, while at least said sharp end of said surgical instrument is covered by said receiver.

18. The method of claim 16, further comprising removing said sharp instrument from said drain after said first end of said drain is outside said patient's body cavity and while said second end of said surgical drain remains inside said patient's body.

19. The method of claim 13, wherein said moving of said receiver and said sharp instrument closer to each other is accomplished by moving said first end and said second end of said safety guide closer to each other.

20. The method of claim 13, further comprising locking said sharp instrument with said receiver.

* * * * *

UNITED STATES PATENT AND TRADEMARK OFFICE
CERTIFICATE OF CORRECTION

| | |
|---|---|
| PATENT NO. | : 6,613,039 B1 |
| APPLICATION NO. | : 09/697463 |
| DATED | : September 2, 2003 |
| INVENTOR(S) | : Robert S. Namba |

It is certified that error appears in the above-identified patent and that said Letters Patent is hereby corrected as shown below:

In Claim 1, Column 11, line 12, change "alumen" to --a lumen--.

Signed and Sealed this

Nineteenth Day of December, 2006

JON W. DUDAS
*Director of the United States Patent and Trademark Office*